United States Patent [19]

Swallow et al.

[11] 4,069,515
[45] Jan. 24, 1978

[54] NON-SLIP THERAPEUTIC STOCKING

[75] Inventors: Roger T. Swallow, Crystal Lake, Ill.; Leonard A. Stanley, Charlotte, N.C.

[73] Assignee: The Kendall Company, Boston, Mass.

[21] Appl. No.: 742,143

[22] Filed: Nov. 15, 1976

Related U.S. Application Data

[62] Division of Ser. No. 676,447, April 13, 1976, Pat. No. 4,021,860.

[51] Int. Cl.² .................. A41B 11/02; A61F 13/08
[52] U.S. Cl. .......................................... 2/239; 36/59 R
[58] Field of Search ............... 2/239, 240, 409, 61; 36/10, 130, 8.3, 59 A, 59 C, 59 R; 66/178 A, 178 R; 128/165

[56] References Cited

U.S. PATENT DOCUMENTS

| 354,232 | 12/1886 | Reid | 36/59 A |
|---|---|---|---|
| 1,395,958 | 11/1921 | Hamilton | 36/59 C |
| 2,771,691 | 11/1956 | Luchs | 36/10 |
| 3,135,442 | 6/1964 | Carter, Jr. | 2/239 X |
| 3,212,103 | 10/1965 | Goodman | 2/409 |
| 3,573,155 | 3/1971 | Mitchell | 36/59 R |
| 3,735,759 | 5/1973 | Mackay | 2/239 X |

Primary Examiner—H. Hampton Hunter
Attorney, Agent, or Firm—Powell L. Sprunger

[57] ABSTRACT

A therapeutic stocking comprising, a boot portion, and a circumferentially elastic foot portion for covering the foot of a patient. The stocking has a lower non-slip region of the foot portion comprising, sheet means of a thermoplastic material fused to the outside of a circumferentially prestretched area of the foot portion underlying the foot. The region is located to contact the floor beneath the patient's foot and provide a relatively high friction surface to minimize slippage of the patient on the floor.

2 Claims, 11 Drawing Figures

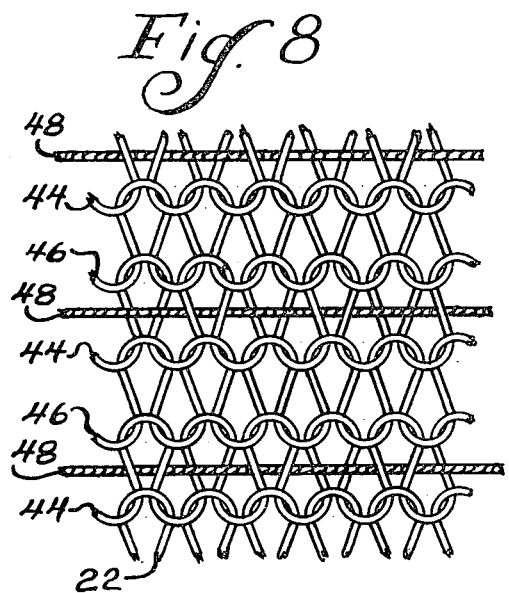
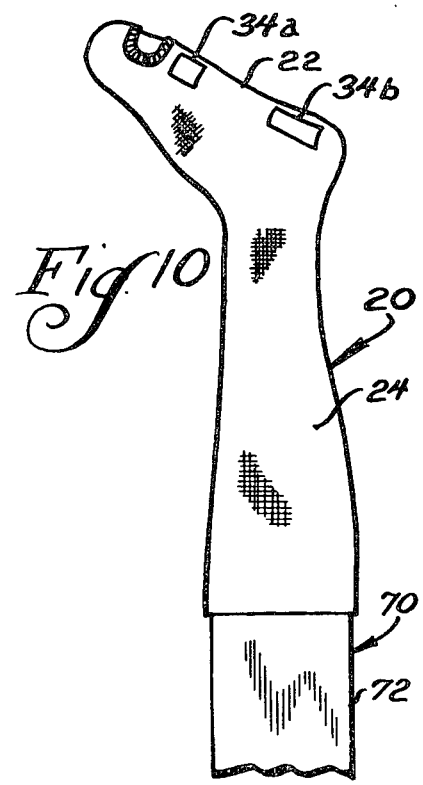
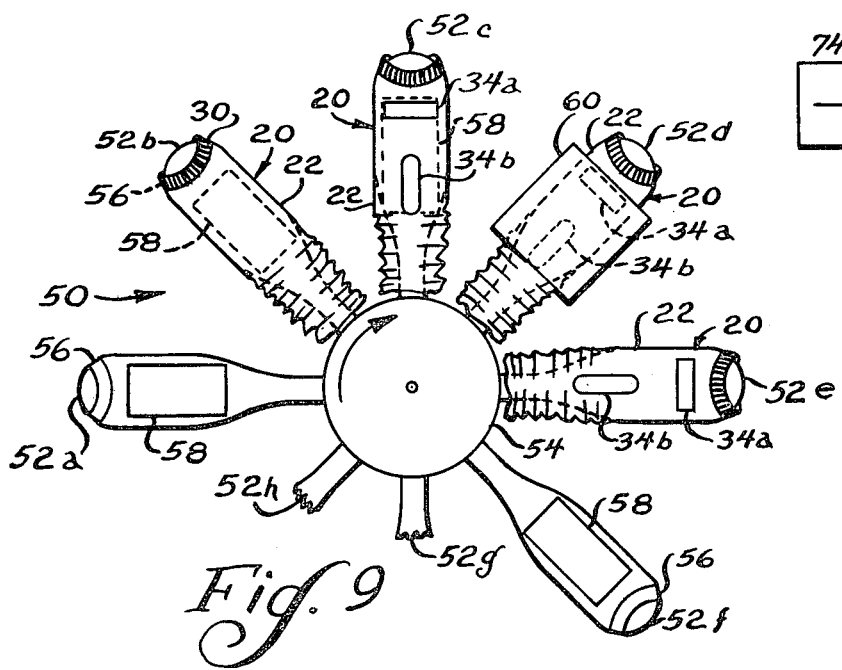
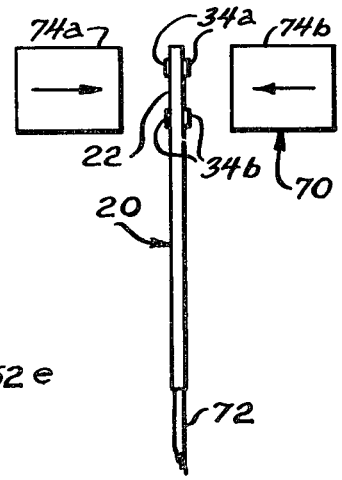

NON-SLIP THERAPEUTIC STOCKING

This is a division of application Ser. No. 676,447, filed Apr. 13, 1976, now U.S. Pat. No. 4,021,860 dated May 10, 1977.

BACKGROUND OF THE INVENTION

The present invention relates to elastic garments, and more particularly to therapeutic stockings.

In the recent past, therapeutic stockings have been prescribed on a relatively wide scale to prevent possible embolism in a patient. When a patient is confined to bed, for example, after an operation, the likelihood of thrombus is markedly increased due to a decrease in the velocity of blood flow in the patient's legs during confinement. Therapeutic or anti-embolism stockings cause application of a compressive pressure against the patient's leg which gradually decreases from the ankle toward the upper part of the leg. Such stockings increase the velocity of blood flow in the legs, and minimize the possibility of thromboembolism.

The stockings are frequently worn in a hospital environment, and are commonly worn by the patients without slippers or shoes. Many of the patients who wear the stockings are relatively weak and unstable on their feet, and it has been found that the patients may slip on the waxed hospital floors while walking or while leaving their beds. It is thus desirable to provide such stockings with a lower surface which prevents slippage on the floors. Since the stockings are periodically laundered, the stockings must be capable of withstanding the elevated temperatures during launderings without loss or degradation of the non-slip surface. Also, the non-slip surface should not impair the desired stretch characteristics of the stocking.

SUMMARY OF THE INVENTION

A principal feature of the present invention is the provision of a therapeutic stocking of simplified construction which minimizes slippage by a patient on a floor.

The stocking of the present invention comprises, a boot portion, and a circumferentially elastic foot portion for covering the foot of the patient. The stocking has a lower non-slip or frictional region of the foot portion comprising, sheet means of a thermoplastic material fused to the outside of a circumferentially prestretched area of the foot portion underlying the foot.

A feature of the present invention is that the region is located to contact the floor beneath the patient's foot and provide a relatively high friction surface to minimize slippage by the patient on the floor.

Another feature of the present invention is that the stocking may be subjected to repeated launderings without degrading the frictional characteristics of the region and without severing the sheet means from the stocking.

Still another feature of the present invention is that the sheet means does not impair circumferential elasticity of the stocking foot portion adjacent the sheet means.

Another feature of the present invention is the provision of a method of forming a non-slip region on the stocking foot portion.

Further features will become more fully apparent in the following description of the embodiments of this invention and from the appended claims.

DESCRIPTION OF THE DRAWINGS

In the drawings:

FIG. 8 is a typical elastic fabric for the stocking foot portion;

FIG. 9 is a schematic view of an apparatus for forming a non-slip region on the stocking foot portion according to a method of the present invention; and FIGS. 10 and 11 are schematic views showing another apparatus for forming the non-slip region according to a method of the present invention.

DESCRIPTION OF THE PREFERRED EMBODIMENTS

Figure 1:
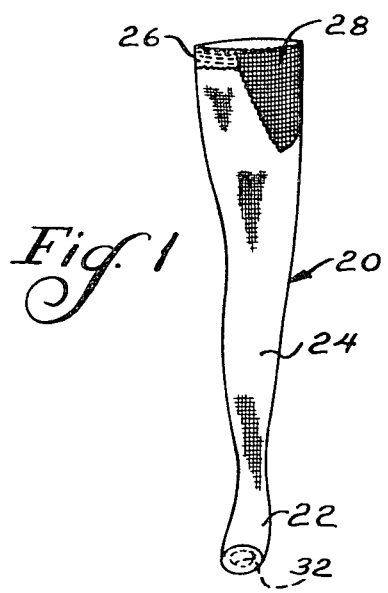
FIG. 1 is a front elevational view of a therapeutic stocking of the present invention.
Figure 2:
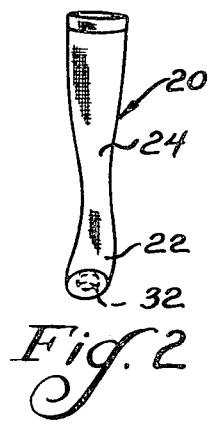
FIG. 2 is a front elevational view of another embodiment of a therapeutic stocking of the present invention.
Figure 3:
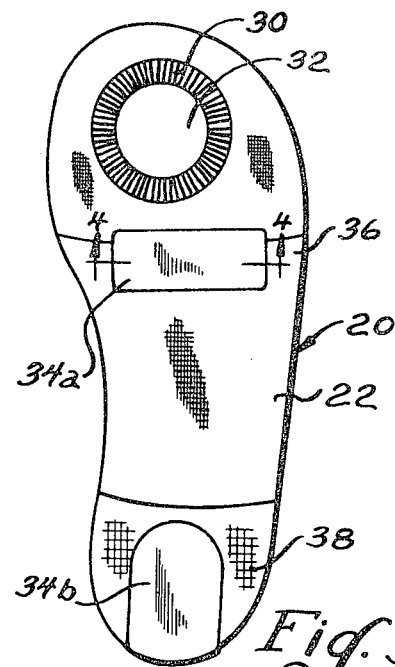
FIG. 3 is a lower plan view of a stocking foot portion showing a non-slip region on the foot portion.

Referring now to FIGS. 1 and 2, there are shown therapeutic stockings generally designated 20 for a patient having a circumferentially elastic foot portion 22 and a circumferentially elastic boot portion 24 extending from the patient's ankle toward the top of the stocking. The foot and boot portions 22 and 24, respectively, may be made from a knitted fabric containing elastomeric yarns to exert a compressive pressure against the patient's leg which gradually decreases from the patient's ankle toward the top of the stocking, although the thigh-length stocking of FIG. 1 may exert a reduced compressive pressure in the region of the knee. The thigh-length stocking of FIG. 1 may also have an elastic band 26 which extends partially around the patient's upper thigh, and which is separated by an area 28 of circumferentially elastic fabric. The stocking of FIG. 2 extends to a location below the patient's knee. As shown in FIGS. 1-3, the stockings 20 may have a welt 30 which defines an opening 32 beneath the patient's toes to permit inspection of the toes while the stockings are worn. In one form, the stocking toe may comprise a non-elastomeric fabric which is attached to the welt 30.

As shown in FIG. 8, the stocking foot portion 22 may have alternating courses of jersey knit stitches of non-elastomeric yarns 44 and 46. The yarns 44 are preferably of Z-twist stretch nylon, such as 70/1, 17 filament Z-twist nylon 66 yarn, while the yarns 46 are preferably of S-twist stretch nylon, such as 70/1, 17 filament S-twist nylon 66 yarn. A covered elastomeric yarn 48, such as a single covered elastomeric yarn having a 280 denier spandex core and a covering of 70/1, 34 filament nylon 6 yarn, is preferably inlaid into every other course of the jersey stitches. The elastomeric yarns may be inlaid into either course of S-twist or Z-twist yarns, as desired. If desired, the elastomeric yarns 48 may be inlaid in every course of the jersey stitches to provide a greater compressive pressure against the foot. Other suitable fabrics may be used for the foot portion 22.

Figure 4:
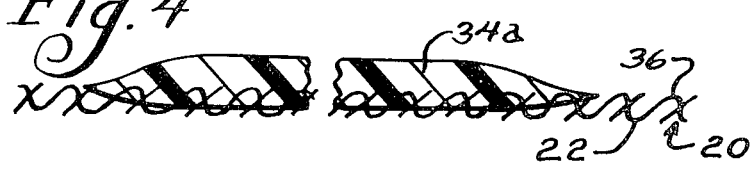
FIG. 4 is a fragmentary sectional view taken substantially as indicated along the line 4—4 of FIG. 3.
Figure 5:
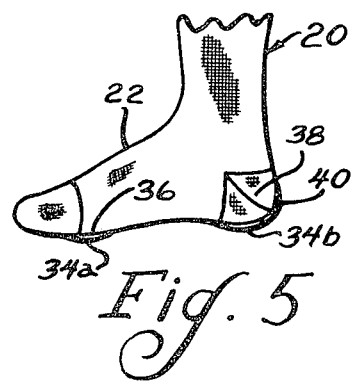
FIG. 5 is a fragmentary side elevational view of the stocking of FIG. 3.

As shown in FIGS. 3-5, the stocking 20 has non-slip regions 34a and 34b positioned on the foot portion 22 beneath the patient's foot and defining an exterior high friction surface for contacting the floor. The lateral region 34a is located adjacent the ball 36 of the patient's foot and adjacent the welt 30. The longitudinal region 34b is located beneath the patient's heel 38, and, as best shown in FIG. 5, includes an end portion extending from beneath the patient's foot upwardly along the back of the patient's heel. Thus, the regions 34a and b are located on raised parts of the foot portion 22 when the stocking is worn in order that the regions contact the floor and minimize slippage by the patient while walking on the floor without slippers or shoes. The end portion 40 of the heel region 34b provides a non-slip surface behind the heel for contacting the floor as the patient leaves a bed.

As will be discussed below, the non-slip regions 34a and b may comprise relatively inelastic strips or sheets of a thermoplastic material which are fused into the fabric of the foot portion 22 in order to bond the strips to the fabric. The strips have a high coefficient of friction relative the stocking fabric, and provide the non-slip surface on the bottom of the stocking foot portion 22. The areas of the foot portion underlying the strips are circumferentially stretched before the strips are bonded to the fabric, such that the strips do not impair the circumferential elasticity of the foot portion adjacent the strips. Thus, after the strips are fused to the fabric and the prestretched fabric is released, the fabric will wrinkle along the sides of the strips and permit stretching of the fabric circumferentially adjacent the strips when the stocking is placed on the patient's foot. The stocking foot portion has a modified two-way stretch, and the foot portion may be stretched slightly in a direction transverse to the circumferential direction prior to attachment of the sheets, if desired. It had been found that the bonded strips withstand repeated launderings without degradation of their frictional characteristics, and do not sever from the stocking during launderings or normal use.

The non-slip strips preferably comprise an internally plasticized thermoplastic material such as a film of vinyl chloride homopolymer sold as Product No. 1-114-1 Plymouth Rubber Company, Inc., Canton, Massachusetts, which is internally plasticized with a 4 to 13 carbon alcohol ester of acids and/or acid anhydrides, containing standard organic stabilizers, fillers, pigments, processing aids and lubricants. Another suitable example of a material for the strips are films sold as product Nos. 981 and S1114-X16 by Harte & Company, Inc., 16 E. 34th Street, New York, New York, which is internally plasticized with diisodecyl phthalate, epoxy plasticizer, polymeric plasticizer, organic-metallic stabilizer and stearic acid lubricant. The films are internally plasticized in order that the plasticizers are not removed during launderings of the stockings, and to provide relatively soft strips which do not have a slippery surface. The films may have a thickness in the range of 4 to 14 mils, preferably approximately 9 mils, and may be colored white. Of course, the strips should be non-toxic, non-irritating, and hypoallergenic.

In an alternative form, the non-slip strips or sheets may be elastic with relative modulii of the strips and the stocking foot portion being such that the strips do not impair or limit expansion of the stocking foot portion when the stocking is worn. Examples of such a material are hear expandable, washfast water based or solvent based coatings or print-on applications of a polyacrylic acid ester and polystyrene latex blend containing a blowing agent and with an expansion ratio of 6 to 12, such as a material sold under the name "Foamcoat" Nos. 50 or 55 by Pierce and Stevens Corporation, 710 Ohio Street, Buffalo, N.Y. Such a material may be applied to the stocking foot portion by screen, roller, or block printing, and are dried and expanded under heat to produce tough non-slip surfaces. Elastic strips may be applied to the stocking foot portion without prestretching the stocking foot portion, if desired.

Figure 6:
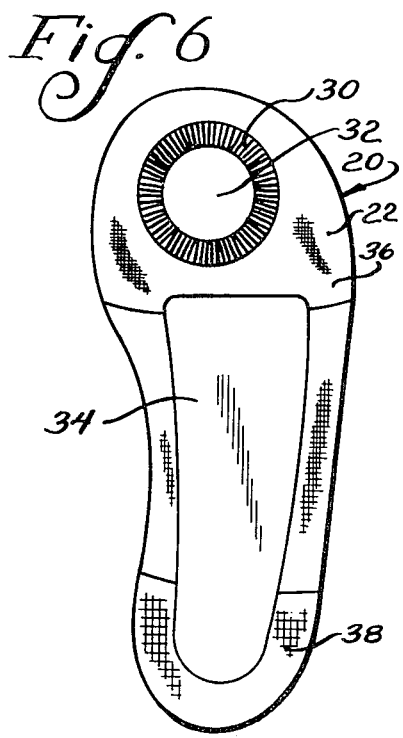
FIG. 6 is a lower plan view of another embodiment of the stocking of the present invention.

Another embodiment of the stocking of the present invention is illustrated in FIG. 6, in which like reference numerals designate like parts. In this embodiment, the foot portion 22 has a welt 30 defining a toe inspection opening 32, as previously described. However, in this embodiment, the region 34 extends from the ball 36 of the patient's foot to the patient's heel 38. As before the region 34 provides a non-slip surface beneath raised parts of the foot when the stocking is worn to minimize slippage by the patient while walking.

Figure 7:
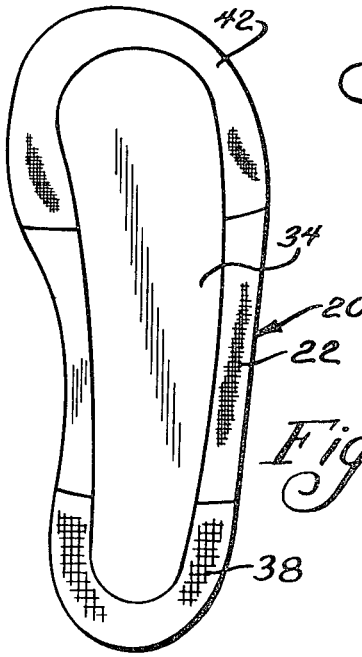
FIG. 7 is a lower plan view of another embodiment of the stocking of the present invention.

Another embodiment of the stocking of the present invention is illustrated in FIG. 7, in which like reference numerals designate like parts. In this embodiment, the non-slip region 34 extends from a location beneath the patient's toes 42 to the heels 38, and extends substantially between the sides of the patient's foot. The region 34 provides a non-slip surface for minimizing slippage by the patient on the floor, in a manner as previously described.

In a suitable example of the stocking of the present invention, strips of the thermoplastic material, sold by Plymouth Rubber Company, Inc., as described above, having a thickness of 9 mils were positioned on the stocking foot portion. The strips were heated to approximately 375° F. while applying a pressure against the strips and fabric of approximately 100 lbs/sq. in. for a time period of approximately 5 seconds. It has been found that if the strips are applied in the absence of sufficient heat, pressure, or time, the strips do not properly bond to the fabric, while if the strips are applied in the presence of an excessive temperature or during an excessive time period, the elastomeric or nylon yarns of the fabric may be destroyed or degraded in function.

Referring now to FIG. 9, there is shown an apparatus generally designated 50 for forming non-slip regions on the stocking foot portion according to a method of the present invention. The apparatus 50 has a plurality of foot forms 52a, b, c, d, e, f, g, and h extending from a central member 54 which is intermittently driven in a clockwise direction and carries the foot forms. As best shown in connection with the foot form 52a, the form has a groove 56 to receive the stocking welt, and has an upper release surface 58, such as a Teflon coated fiberglas fabric, such as the product Fluorglas 2815-6, sold by Dodge Industries, Inc. of Hoosick Falls, N.Y. As shown in connection with the foot form 52b, the stocking is placed on the form before or after boarding with the welt 30 being located in the form groove 56, and with the lower part of the foot portion 22 being located above the release surface 58. The foot forms are sufficiently wide to circumferentially stretch the stocking foot portions 22 when they are placed on the foot forms.

As illustrated in connection with the foot form 52c, the thermoplastic strips 34a and 34b are placed at the desired position on top of the lower part of the stocking foot portion 22 and above the release surface 58 of the foot form. As shown in connection with the foot form 52d, the apparatus 50 has a heating member 60 which is preferably coated with a release surface or tetrafluorethylene, such as Teflon, a trademark of E. I. du Pont de Nemours, and which is movable between a position spaced above the stocking and a position bearing against the thermoplastic strips 34a and b and the foot form, such that the thermoplastic strips and stocking are compressed between the heating member 60 and the foot form 52d. Thus, when the foot form supporting the thermoplastic strips moves to a location below the heating member and rotation of the central member 54 has been stopped, the heating member 60 moves to its lower position engaging against the thermoplastic strips 34a and b. The heating member 60 applies heat and pressure to the thermoplastic strips during a period of time in order to fuse the strips into the fabric of the stocking foot portion, after which the heating member 60 moves to its spaced upper position. The release surface 58 prevents bonding of the thermoplastic material to the foot form, while the foot form itself separates the foot portion and prevents bonding of the material to the upper part of the stocking foot portion below the foot form. As shown in connection with the foot form 52e, the completed stocking has the thermoplastic strips 34a and b fused into the stocking fabric, and the stocking may be removed from the foot forms at this time, as will be seen in connection with the empty foot form 52f.

Thus, the apparatus 50 intermittently rotates the foot forms, and the stockings may be positioned on the forms when they are stopped at the location of the foot form 52b, 52f, 52g, 52h, or 52a. As the apparatus rotates to its next position, the thermoplastic strips may be placed on the stocking foot portion, after which the stocking foot portion containing the thermoplastic strips rotates to a position beneath the heating member where the thermoplastic strips are fused to the stocking foot portion. Finally, the heating member raises from the stocking, and the stocking foot portion containing the fused strips rotates to the position shown in connection with the foot form 52e, where the completed stockings may be removed form the foot forms.

Another device generally designated 70 for applying the thermoplastic strips to the stocking foot portion according to a method of the present invention is illustrated in FIGS. 10 and 11. As shown, the stocking 20 is placed on a boarding form 72, and separate strips of thermoplastic material 34a and 34b are positioned on opposite sides of the boarding form against the stocking foot portion 22. The strips 34a and b may be retained at their desired position by suitable means, such as by adhesive on the strips. Next, as shown in FIG. 11, a pair of opposed heating members 74a and 74b are moved toward the thermoplastic strips 34a and b. The heating members 74a and b apply heat and pressure to the strips 34a and b between the heating members and the boarding form 72 for a period of time, after which the heating members 74a and b are moved away from the stocking containing the fused strips. Although the strips are shown as being retained on the stocking foot portion before being fused to the fabric, it will be apparent that the strips may be retained on the heating members 74a and b by suitable means before being fused, such as by a source of vacuum. Additionally, the boarding form 72 may have a release surface underlying the thermoplastic strips and the heating members 74a and b may have suitable release surfaces to prevent bonding of the thermoplastic strips to the boarding form and the heating members, in a manner as previously described. The device 70 may be utilized to fuse the thermoplastic strips to the stocking foot portion either before boarding, during boarding, or after boarding, as desired.

Thus, according to a method of the present invention, a lower area of the stocking foot portion is stretched in a circumferential and/or longitudinal direction, the strips of thermoplastic material are positioned in the stretched area on the outside of the foot portion, and heat and pressure are applied to the strips during a period of time to fuse the strips to a region of the foot portion. Although in a preferred form the non-slip strips are fused to the stocking foot portion, it is apparent that the strips, whether elastic, inelastic, or a thermoplastic material, may be attached to the stocking by other suitable means, such as by sewing or adhesive.

The foregoing detailed description is given for clearness of understanding only, and no unnecessary limitations should be understood therefrom, as modifications will be obvious to those skilled in the art.

We claim:

1. A therapeutic foot covering garment for use without shoes comprising, a foot portion for covering the foot of a patient, said foot portion being circumferentially elastic to conform to the shape of the patient's foot, and an elastic strip of non-slip high friction material attached to a region of the foot portion underlying the foot, said strip having sufficient elasticity to prevent impairment of the foot portion elasticity when the stocking is worn, and said strip being located to contact the floor beneath the patient's foot and minimize slippage of the patient on the floor.

2. The garment of claim 1 wherein the strip comprises a polyacrylic acid ester and polystyrene latex blend containing a blowing agent with an expansion ratio of from 6 to 12.

* * * * *